United States Patent
Aliyev et al.

(10) Patent No.: US 8,653,316 B2
(45) Date of Patent: Feb. 18, 2014

(54) PROCESS FOR THE PREPARATION OF LINEAR ALPHA-OLEFINS AND CATALYST USED THEREIN

(75) Inventors: Vugar O. Aliyev, Riyadh (SA); Atieh Abu-Raqabah, Riyadh (SA); Mohammad Zahoor, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 1076 days.

(21) Appl. No.: 11/990,173

(22) PCT Filed: Aug. 10, 2006

(86) PCT No.: PCT/IB2006/002185
§ 371 (c)(1),
(2), (4) Date: Feb. 23, 2009

(87) PCT Pub. No.: WO2007/026200
PCT Pub. Date: Mar. 8, 2007

(65) Prior Publication Data
US 2009/0306449 A1    Dec. 10, 2009

(30) Foreign Application Priority Data

Aug. 31, 2005 (EP) ................................ 05018878

(51) Int. Cl.
*C07C 2/22* (2006.01)
*B01J 31/04* (2006.01)

(52) U.S. Cl.
USPC .......... 585/523; 502/103; 502/117; 502/118; 502/122; 502/125; 502/127; 585/520; 585/521; 585/522

(58) Field of Classification Search
USPC ........... 585/500, 502, 520, 521, 522, 523; 502/100, 102, 103, 118, 121, 122, 123, 502/125, 126, 127, 117
See application file for complete search history.

(56) References Cited

U.S. PATENT DOCUMENTS

| | | | | |
|---|---|---|---|---|
| 3,862,257 | A * | 1/1975 | Buben et al. | 585/523 |
| 4,361,714 | A | 11/1982 | Langer et al. | |
| 4,409,409 | A | 10/1983 | Langer, Jr. et al. | |
| 4,442,309 | A | 4/1984 | Langer, Jr. | |
| 4,486,615 | A * | 12/1984 | Langer, Jr. | 585/523 |
| 4,783,573 | A | 11/1988 | Shiraki et al. | |
| 4,855,525 | A * | 8/1989 | Young et al. | 585/523 |
| 5,260,500 | A | 11/1993 | Shiraki et al. | |
| 5,292,979 | A * | 3/1994 | Chauvin et al. | 585/523 |
| 5,349,115 | A * | 9/1994 | Nomura et al. | 585/513 |
| 5,496,783 | A | 3/1996 | Chauvin et al. | |
| 6,121,502 | A * | 9/2000 | Tembe et al. | 585/524 |
| 6,372,684 | B1 | 4/2002 | Horton et al. | |
| 6,930,218 | B2 * | 8/2005 | Tembe et al. | 585/523 |
| 2002/0147375 | A1 | 10/2002 | Tembe et al. | |

FOREIGN PATENT DOCUMENTS

| | | |
|---|---|---|
| DE | 198 12 066 A1 | 1/1999 |
| JP | 7330633 A | 12/1995 |
| JP | 7330634 A | 12/1995 |
| JP | 2002255863 A | 9/2002 |
| WO | WO8000224 A1 | 2/1980 |
| WO | WO 91/02707 | 3/1991 |

OTHER PUBLICATIONS

German Patent No. 19812066 (A); Publication Date: Jan. 7, 1999; Abstract Only; 1 Page.
International Publication No. 8000224 (A); Date of Publication: Feb. 21, 1980; Abstract Only; 1 Page.
International Search Report; International Application No. PCT/IB2006/002185; International Filing Date: Aug. 10, 2006; Date of Mailing: Feb. 6, 2007; 2 Pages.
Written Opinion of the International Searching Authority; International Application No. PCT/IB2006/002185; International Filing Date: Aug. 10, 2006; Date of Mailing: Feb. 6, 2007; 5 Pages.
Japanese Patent No. 2002255863 (A); Publication Date: Sep. 11, 2002; Abstract Only; 1 Page.
Japanese Patent No. 7330633 (A); Publication Date: Dec. 19, 1995; Abstract Only; 1 Page.
Japanese Patent No. 7330634 (A); Publication Date: Dec. 19, 1995; Abstract Only; 1 Page.

* cited by examiner

*Primary Examiner* — In Suk Bullock
*Assistant Examiner* — Bradley Etherton
(74) *Attorney, Agent, or Firm* — Cantor Colburn LLP

(57) ABSTRACT

The present invention relates to a process for the preparation of linear low molecular weight alpha-olefins having 4 to 24 carbon atoms, comprising oligomerizing ethylene in an inert solvent in the presence of a catalyst system comprising: (i) zirconium carboxylate of the formula $(R^1COO)_m ZrCl_{4-m}$, wherein $R^1$ is saturated or unsaturated aliphatic $C_1$-$C_{10}$ hydrocarbon or aromatic $C_6$-$C_{14}$ hydrocarbon and m fulfills $1 \le m \le 4$, (ii) at least one aluminum compound selected from organoaluminum compounds of the formula $R^2_n AlX_{3-n}$, wherein $R^2$ is $C_1$-$C_{20}$ alkyl, X is chlorine, bromine or iodine, and n fulfills $1 \le n \le 2$, and/or aluminoxanes, and (iii) at least two different additives selected from the group consisting of hydrogen, esters, ketones, ethers, amines, anhydrides, phosphines and sulfur compounds; as well as to a catalyst used therein.

15 Claims, No Drawings

PROCESS FOR THE PREPARATION OF LINEAR ALPHA-OLEFINS AND CATALYST USED THEREIN

The present invention relates to a process for the preparation of linear alpha-olefins and a catalyst used therein.

Linear alpha-olefins having 4 to 24 carbon atoms, preferably 4 to 20 carbon atoms, more preferably 6 to 18 carbon atoms are key feedstocks in the production of surfactants, plasticizers, synthetic lubricants and polyolefins. Alpha-olefins of high purity are particularly valuable in the production of linear low density polyethylene and in the oxo process. In this regard, linear alpha-olefins having 6 to 18 carbon atoms are particularly useful and are required widely in large quantities.

Although linear olefins are the product of dehydrogenation of linear alkanes, the major portion of such products consists of the internal olefins. Therefore, the preparation of alpha-olefins is largely based on the oligomerization of ethylene.

These linear alpha-olefins are usually prepared by catalytic oligomerization of ethylene in the presence of a Ziegler-Natta-type catalyst. The key factor in ethylene oligomerization is to get the desired selectivity, product distribution and purity of the alpha-olefins obtained. Catalyst and process conditions play an important role. Various types of catalysts are known to be suitable for that purpose including, for example, a binary catalyst system comprising an ethylaluminumchloride combined with titanium tetrachloride, optionally with further admixture of a third ingredient for enhancing the selectivity.

The above-mentioned catalyst systems using a titanium compound are not quite satisfactory in respect of activity and selectivity of the catalyst.

On the other hand, binary catalysts with increased activities have been proposed comprising zirconium instead of titanium. The use of zirconium containing catalysts is, for example, disclosed in U.S. Pat. Nos. 4,361,714; 4,409,409; 4,442,309; 4,783,573; 4,855,525; 5,260,500; 6,372,684; and 20020147375.

For example, a catalyst for the oligomerization of ethylene to linear $C_4$-$C_{30}$ alpha-olefins is known including zirconium tetrachloride and an organoaluminum compound. The oligomerization of that known catalyst is usually performed in a medium of hydrocarbon solvents at temperatures of about 100 to about 150° C. and at elevated pressures of 4-8 MPa.

However, the main disadvanages of that known catalyst are the poor solubility of zirconium tetrachloride in hydrocarbon solvents, the severe conditions for operation of the catalyst and its relatively low selectivity. In the course of oligomerization of ethylene, a large amount of wax and polymer up to 3.0 wt. % of high molecular polyethylene are formed together with the linear alpha-olefins.

Further, WO80/00224 also teaches a catalyst which includes a zirconium carboxylate of the general formula $(RCOO)_m ZrCl_4$, and an organoaluminum compound of the formula $R_n AlX_{3-n}$. The main disadvantages of that catalyst system is the formation of undesired and problematic by-products such as oligomers of $C_{20+}$ and also polyethylene polymer. The formation of heavy oligomers which are waxy solids and only partly soluble in the product mix of linear alpha-olefins causes reactor plugging and consequently the reactor has frequently to shut down for cleaning.

The formation of wax and/or polymers, even in small amounts, adversely affects the entire technological process on producing oligomers, since by-products not only lower the yield of desired oligomers and its purity, but also reduce the working time of the process equipment, insofar as solid polymer accumulating in the reactors has to be periodically removed which can be only done by interrupting the oligomerization process and, hence, at the expense of lost time of equipment.

Consequently, there is a need to develop a new process and a new catalyst system which can provide at least equivalent or even greater catalytic activity and allows at the same time to eliminate all problems mentioned above.

It is therefore the object of the present invention to provide a process for the preparation of linear low molecular weight alpha-olefins which overcomes the drawbacks of the prior art, especially to provide a process providing linear alpha-olefins with improved selectivity, purity and without formation of waxy or polymeric by-products.

It is a further object of the invention to provide a catalyst which may be utilized in such a process.

This object is achieved by a process for the preparation of linear low molecular weight alpha-olefins having 4 to 24 carbon atoms, comprising oligomerizing of ethylene in an inert solvent in the presence of a catalyst system comprising: (i) zirconium carboxylate of formula $(R^1COO)_m ZrCl_{4-m}$, wherein $R^1$ is saturated or unsaturated aliphatic $C_1$-$C_{10}$ hydrocarbon or aromatic $C_6$-$C_{14}$ hydrocarbon and m fulfills $1 \leq m \leq 4$, (ii) at least one aluminum compound selected from organoaluminum compounds of the formula $R^2{}_n AlX_{3-n}$, wherein $R^2$ is $C_1$-$C_{20}$ alkyl, X is chlorine, bromine or iodine, and n fulfills $1 \leq n \leq 2$, and/or aluminoxanes, and (iii) at least two different additives selected from the group consisting of hydrogen, esters, ketones, ethers, amines, anhydrides, phosphines and sulfur compounds.

In one embodiment, linear low molecular weight alpha-olefins having 4 to 20 carbon atoms, preferably 4 to 18 carbon atoms, are prepared.

Preferably, the solvent is an aromatic hydrocarbon, an aliphatic hydrocarbon, an alicyclic hydrocarbon or mixtures thereof.

More preferably, the solvent is selected from the group consisting of toluene, benzene, xylene, chlorobenzene, dichlorobenzene, chlorotoluene, pentane, hexane, heptane, octane, nonane, decane, cyclohexane, decahydronaphthalene, dichloroethane, dichlorobutane or mixtures thereof.

It is preferred that the oligomerization is carried out at a temperature of about 50 to about 110° C., preferably at about 55° C. to about 75° C.

In one embodiment, the oligomerization is carried out at a pressure of about 10 to about 50 barg, preferably about 20 to about 40 barg.

The second object is achieved by a catalyst system comprising (i) zirconium carboxylate of the formula $(R^1COO)_m ZrCl_{4-m}$, wherein $R^1$ is saturated or unsaturated aliphatic $C_1$-$C_{10}$ hydrocarbon or aromatic $C_6$-$C_{14}$ hydrocarbon and m fulfills $1 \leq m \leq 4$, (ii) at least one aluminum compound selected from organoaluminum compounds of the formula $R^2{}_n AlX_{3-n}$, wherein $R^2$ is $C_1$-$C_{20}$ alkyl, X is chloride, bromide or iodide, and n fulfills $1 \leq n \leq 2$, and/or aluminoxanes and (iii) at least two different additives selected from the group consisting of hydrogen, esters, ketones, ethers, amines, anhydrides, phosphines and sulfur compounds.

Preferably, the zirconium carboxylate is $Zr(i$-$C_3H_7COO)_4$ and/or the aluminum compound is ethylaluminum sesquichloride.

The at least two additives may be selected from the group consisting of methyl acetate, methyl acetoacetate, ethyl acetate, ethyl acetoacetate, methyl benzoate, ethyl benzoate, anisol, thiophene, thioanisol, thiophene-2-carboxyaldehyde, thiophene-2-methanol, thiophenol, diphenylsulfide, dibenzoylthiophene, methanol, ethanol, tetrahydrofuran (THF), 1,4-dioxane, diethylether, methyl tert-butylether, triethylamine, cyclopentylamine, aniline, triphenylphosphine, triethylphosphine, acetone, methylethylketone, acetaldehyde, carbon disulfide, dimethylsulfoxide, acetonitrile, pyridine, or mixtures thereof.

Most preferably, the at least two additives are selected from the group consisting of ethyl acetate, ethylacetoacetate, ethyl benzoate, anisol, thiophenol, thiophene, tetrahydrofuran (THF), cyclopentylamine or mixtures thereof.

In one embodiment, the molar ratio of the aluminum compound to zirconium compound is about 1:1 to about 70:1, preferably about 10:1 to about 50:1.

In a further embodiment, the molar ratio of the sum of the at least two additives to the zirconium compound is about 0.01 to about 25, preferably 0.1 to about 3.

Preferably, the molar ratio of the at least two additives is about 1:10 to about 10:1.

The inventive catalyst system may be used in a process for the preparation of low molecular weight linear alpha-olefins having $C_4$ to $C_{24}$ carbon atoms Surprisingly, it was found that the inventive process especially improves the purity of the linear alpha-olefins obtained, wherein the selectivity of the catalyst system used in that process is kept on a high level. Additionally, linear alpha-olefins are obtained in that process without the formation of wax or polymer. Thus, the inventive process may be advantageously utilized considering reduced reactor shutdowns and cost-savings. Without wishing to be bound to any theory, it seems that the use of at least two of the additives, such as electron donors, results in a synergistic effect.

Additionally, a mixture of the solvents may be used to control the product molecular weight distribution to obtain maximum selectivity of the desired olefin products.

The catalyst components can be combined prior to their introduction into the reaction vessel, or the catalyst system may be formed in situ in the reactor. According to the present invention, there is no particular limitation on the method of preparing the catalyst system from components (i), (ii) and (iii). There is additionally no limitation of the order of addition of the catalyst components.

The invention will now become apparent from the following detailed description of preferred embodiments of the invention by means of examples.

EXAMPLES

All materials were handled in a nitrogen atmosphere using either schlenk techniques or nitrogen filled glove box. Nitrogen and toluene were supplied from a plant source and were dried through an additional bed of molecular sieves, if necessary.

The synthesis of zirconium carboxylates were performed according to known methods in the art. The oligomerization of ethylene was performed as follows.

The prepared catalyst solution was charged into a 2 liter batch reactor. Ethylene was introduced into the reactor until the desired pressure was obtained and maintained throughout the reaction at the desired temperature. Ethylene was delivered on demand in an amount necessary to maintain the predetermined reaction pressure. After the reaction was continued for one hour with maintaining the reacting conditions, the reaction was stopped by adding about 20 ml ethanol to the reaction mixture. The linear alpha-olefin product obtained was separated, collected and analyzed by gas chromatography. The yield of fractions, as given in table 1 below, was estimated from the Schulz-Flory distribution. Results for the distribution of alpha-olefins (wt %, fractions) and the purity of the fractions obtained are given in tables 1 and 2 below.

The following examples are given to illustrate the subject-matter of the present invention. As will be apparent to those skilled in the art, numerous changes and modifications are possible, and thus the scope of the invention should not be limited thereto.

Comparative Example 1

0.25 mmol $Zr(i-C_3H_7COO)_4$ were added into a reactor with 250 ml toluene and then 0.125 mmol ethyl acetate was added, followed by the addition of neat ethylaluminum sesquichloride EASC (Al/Zr=17.5) to the mixture. The reaction was conducted at 80° C. and 30 bar ethylene pressure. The oligomerization time was 60 minutes. After that, the oligomerization process was stopped by adding about 20 ml ethanol and 249 g of linear alpha-olefins were obtained. The yield of linear alpha-olefins LAO was 10921 g LAO/g Zr obtained as a clear liquid. Traces of solid polymer were detected.

Comparative Example 2

The same procedure as in example 1 was repeated, except that 0.125 mmol ethyl acetoacetate was added to the mixture. 255 g of LAO was formed as a clear liquid with a yield of 11184 g LAO/g Zr. Traces of solid polymer were detected.

Comparative Example 3

The same procedure as in example 1 was repeated, except that 0.125 mmol ethyl benzoate was added to the mixture. 229 g of LAO was formed; a yield of 10.043 g LAO/g Zr. Traces of solid polymer were detected.

Comparative Example 4

The same procedure as in example 1 was repeated, except that 0.037 mmol cyclopentylamine was added to the mixture. 240 g of LAO was formed in the process; a yield of 10526 g LAO/g Zr. Traces of solid polymer were detected.

Example 5

250 ml toluene was placed in a 300 ml round bottom flask and 0.25 mmol Zr $(i-C_3H_7COO)_4$ was added to the flask. Then 0.125 mmol ethyl acetoacetate was added, followed by the addition of neat EASC (Al/Zr=17.5). Then 0.5 mmol thiophene was added to the mixture. The prepared catalyst solution was then charged into a 2 liter reactor. A reaction was conducted at 70° C. and 30 bar ethylene pressure. The oligomerization time was 60 minutes. Finally, 216 g of LAO was formed; a yield of 9473 g LAO/g Zr. No wax or polymer was formed.

Example 6

250 ml toluene was placed in a 300 ml round bottom flask and 0.25 mmol Zr $(i-C_3H_7COO)_4$ was added to the flask. Then 0.125 mmol ethyl acetoacetate was added, followed by the addition of 0.5 mmol thiophene. Then neat EASC (Al/Zr=17.5) was added to the mixture. The reaction was conducted at 70° C. and 25 bar ethylene pressure. The oligomerization time was 60 minutes. 193 g of LAO was formed; a yield of 8465 g LAO/g Zr. No wax or polymer was formed.

Comparative Example 7

250 ml toluene, 0.25 mmol of $Zr(i-C_3H_7COO)_4$ and neat EASC (Al/Zr=35) were mixed in a 300 ml round bottom flask. The reaction was conducted at 80° C. and 30 bar ethylene pressure. The oligomerization time was 60 minutes. 213 g of LAO was formed; yield 9342 g of LAO/g Zr. Traces of solid polymer were detected.

Comparative Example 8

The same procedure as in Comparative example 7 was repeated, except that a ratio of Al/Zr=17.5 was used. The reaction was conducted at 80° C. and 30 bar ethylene pressure. The oligomerization time was 60 minutes. 460 g of LAO and 0.2 g of polyethylene by-product were obtained; a yield of 20175 g LAO/g Zr.

Comparative example 9

250 ml toluene was placed in a 300 ml round bottom flask and 0.25 mmol $Zr(i-C_3H_7COO)_4$ was added into the flask. Then neat EASC (Al/Zr=17.5) was added, followed by the addition of 0.5 mmol thiophene to the mixture. The reaction was conducted at 80° C. and 30 bar ethylene pressure. The oligomerization time was 60 minutes. 378 g of LAO were obtained as a milky liquid; a yield of 16579 g of LAO/g Zr. Traces of solid polymer were detected.

Comparative Example 10

0.25 mmol $Zr(i-C_3H_7COO)_4$ were added to 250 ml toluene into a reactor, and then 0.5 mmol THF was added followed by the addition of neat EASC (Al/Zr=35) to the mixture. The reaction was conducted at 80° C. and 30 bar ethylene pressure. The oligomerization time was 60 minutes. 290 g of LAO were obtained; a yield of 12719 g of LAO/g Zr. The linear alpha-olefins were obtained as clear liquid. Traces of solid polymer were detected.

Comparative Example 11

0.25 mmol $Zr(i-C_3H_7COO)_4$ were added to 250 ml toluene in the reactor, and then 0.5 mmol 1,4-dioxane was added followed by the addition of neat EASC (Al/Zr=35) to the mixture. The reaction was conducted at 80° C. and 30 bar ethylene pressure. The oligomerization time was 60 minutes. 275 g of LAO were obtained; a yield of 12061 g of LAO/g Zr, which were obtained as a clear liquid. Traces of solid polymer were detected.

As can be seen from the examples and comparative examples, examples 5 and 6 result in the best results regarding purity of the LAO fractions obtained. The linear alpha-olefins obtained in examples 5 and 6 do not comprise any wax or polymer.

TABLE 1

| Examples | Distribution of alpha olefins (wt %) | | | |
|---|---|---|---|---|
| | C4 | C6-C10 | C12-C18 | C20+ |
| Comparative Example 1 | 38.2 | 40 | 19.6 | 2.2 |
| Comparative Example 2 | 39.4 | 40.3 | 18.5 | 1.8 |
| Comparative Example 3 | 38 | 39.8 | 19.1 | 3.1 |
| Comparative Example 4 | 38.7 | 40.7 | 19 | 1.6 |
| Example 5 | 38.5 | 46.2 | 15.3 | 0 |
| Example 6 | 32.5 | 42.9 | 24.3 | 0.3 |

TABLE 1-continued

| Examples | Distribution of alpha olefins (wt %) | | | |
|---|---|---|---|---|
| | C4 | C6-C10 | C12-C18 | C20+ |
| Comparative Example 7 | 35.1 | 45.8 | 17.4 | 1.7 |
| Comparative Example 8 | 15 | 30.4 | 40.9 | 13.7 |
| Comparative Example 9 | 14.9 | 45.1 | 30.9 | 9.1 |
| Comparative Example 10 | 36.1 | 44.8 | 17.9 | 1.2 |
| Comparative Example 11 | 40.5 | 45.7 | 12.9 | 0.9 |

TABLE 2

| Examples | Purity of LAO fractions (%) | | | | | | | |
|---|---|---|---|---|---|---|---|---|
| | C4 | C6 | C8 | C10 | C12 | C14 | C16 | C18 |
| Comparative Example 1 | 99.1 | 97.9 | 96.1 | 93.2 | 93.1 | 90.8 | 90.1 | 88.1 |
| Comparative Example 2 | 98.7 | 97.6 | 95.5 | 92.8 | 91.6 | 89.5 | 90.8 | 87.9 |
| Comparative Example 3 | 99.1 | 97.8 | 95.8 | 92.7 | 92.1 | 90.1 | 88.5 | 87.8 |
| Comparative Example 4 | 98.8 | 97.3 | 95.4 | 91.6 | 90.1 | 86.3 | 84.2 | 83.5 |
| Example 5 | 99.3 | 98.1 | 97.1 | 95.7 | 95.5 | 93.8 | 93.4 | 93.3 |
| Example 6 | 98.9 | 97.9 | 96.1 | 94.1 | 93.9 | 92.1 | 91.5 | 90.8 |
| Comparative Example 7 | 98.2 | 96.1 | 95 | 88.2 | 86 | 83.4 | 84 | 80.3 |
| Comparative Example 8 | 98.1 | 97.1 | 94.8 | 91.1 | 90.5 | 87.2 | 79.1 | 77.4 |
| Comparative Example 9 | 98.3 | 97 | 95.3 | 91.8 | 91.3 | 86.5 | 83.3 | 82.6 |
| Comparative Example 10 | 98.4 | 96.2 | 94.9 | 88.2 | 87.2 | 85.2 | 83.8 | 81 |
| Comparative Example 11 | 98.7 | 96.5 | 93.7 | 88.7 | 88.6 | 86.2 | 82.1 | 80.5 |

The features disclosed in the foregoing description and in the claims may, both separately and in any combination thereof, be material for realizing the invention in diverse forms thereof.

The invention claimed is:

1. A process for the preparation of linear low molecular weight alpha-olefins having 4 to 24 carbon atoms, comprising oligomerizing of ethylene in an inert solvent in the presence of a catalyst system comprising:
   (i) zirconium carboxylate of the formula $(R^1COO)_mZrCl_{4-m}$, wherein $R^1$ is saturated or unsaturated aliphatic $C_1$-$C_{10}$ hydrocarbon or aromatic $C_6$-$C_{14}$ hydrocarbon and m fulfills $1 \leq m \leq 4$,
   (ii) at least one aluminum compound selected from organoaluminum compounds of the formula $R^2{}_nAlX_{3-n}$, wherein $R^2$ is $C_1$-$C_{20}$ alkyl, X is chlorine, bromine or iodine, and n fulfills $1 \leq n \leq 2$, and/or aluminoxanes, and
   (iii) an ester compound and a sulphur compound.

2. The process according to claim 1, wherein said two additives are ethyl acetoacetate and thiophene.

3. The process according to claim 1, wherein linear low molecular weight alpha-olefins having 4 to 20 carbon atoms are prepared.

4. The process according to claim 3, wherein linear low molecular weight alpha-olefins having 4 to 18 carbon atoms, are prepared.

5. The process according to claim 1, wherein the solvent is an aromatic hydrocarbon, an aliphatic hydrocarbon, an alicyclic hydrocarbon or mixtures thereof.

6. The process according to claim 5, wherein the solvent is selected from the group consisting of toluene, benzene, xylene, chlorobenzene, dichlorobenzene, chlorotoluene, pentane, hexane, heptane, octane, nonane, decane, cyclohexane, decahydronaphthalene, dichloroethane, dichlorobutane or mixtures thereof.

7. The process according to claim 1, wherein the oligomerization is carried out at a temperature of 50 to 110° C.

8. The process according to claim 1, wherein the oligomerization is carried out at a pressure of 10 to 50 bar.

9. A catalyst system comprising
 (i) zirconium carboxylate of the formula $(R^1COO)_m ZrCl_{4-m}$, wherein $R^1$ is saturated or unsaturated aliphatic $C_1$-$C_{10}$ hydrocarbon or aromatic $C_6$-$C_{14}$ hydrocarbon and m fulfills $1 \leq m \leq 4$,
 (ii) at least one aluminum compound selected from organoaluminum compounds of the formula $R^2_n AlX_{3-n}$, wherein $R^2$ is $C_1$-$C_{20}$ alkyl, X is chloride, bromide or iodide, and n fulfills $1 \leq n \leq 2$, and/or aluminoxanes, and
 (iii) an ester compound and a sulphur compound.

10. The catalyst system according to claim 9, wherein said two additives are ethyl acetoacetate and thiophene.

11. The catalyst system according to claim 9, wherein the zirconium carboxylate is $Zr(i-C_3H_7COO)_4$.

12. The catalyst system according to claim 9, wherein the aluminum compound is ethylaluminum sesquichloride.

13. The catalyst system according to claim 9, wherein the molar ratio of the aluminum compound to zirconium compound is 1:1 to 70:1.

14. The catalyst system according to claim 9, wherein the molar ratio of the sum of the at least two additives to the zirconium compound is 0.01 to 25.

15. The catalyst system according to claim 9, wherein the molar ratio of the at least two additives is 1:10 to 10:1.

\* \* \* \* \*